United States Patent [19]

van't Riet et al.

[11] 4,448,730

[45] May 15, 1984

[54] HYDROXYBENZOHYDROXAMIC ACIDS, BENZAMIDES AND ESTERS AND RELATED COMPOUNDS AS RIBONUCLEOTIDE REDUCTASE INHIBITORS

[76] Inventors: Bartholomeus van't Riet, 3419 Noble Ave., Richmond, Va. 23222; Howard L. Elford, 3313 Gloucester Rd., Richmond, Va. 23227; Galen L. Wampler, 6938 Chamberlayne Rd., Mechanicsville, Va. 23111

[21] Appl. No.: 370,023

[22] Filed: Apr. 20, 1982

Related U.S. Application Data

[63] Continuation-in-part of Ser. No. 247,171, Mar. 24, 1981, Pat. No. 4,394,389 which is a continuation-in-part of Ser. No. 16,472, Mar. 1, 1979, Pat. No. 4,263,322

[51] Int. Cl.$^3$ .................... C07C 83/08; C07C 69/88
[52] U.S. Cl. ................ 260/500.5 H; 560/70; 560/75; 562/476; 564/170; 424/308; 424/315; 424/324
[58] Field of Search .................. 560/70, 75; 260/500.5 H; 424/308, 345, 324; 564/170

[56] References Cited

U.S. PATENT DOCUMENTS

| 2,849,480 | 8/1958 | Krenchmann | 260/473 |
| 3,422,141 | 1/1969 | Comodi | 564/170 |
| 4,263,322 | 4/1981 | van't Riet | 260/500.5 H |

FOREIGN PATENT DOCUMENTS

| 314060 | 1/1969 | Sweden | 564/170 |
| 345016 | 4/1960 | Switzerland | 564/170 |

OTHER PUBLICATIONS

Gale, *Proc. Soc. Exptl. Biol. Med.*, 122, 1236 (1966).
Gale & Hynes, *J. Med. Chem.*, 11, 191 (1968).
Howle & Gale, *Proc. Soc. Exptl. Biol., Med.*, 131, 697 (1969).
Gale, Hynes & Smith, *J. Med. Chem.*, 14, 571 (1970).
Gale & Carnes, *Clin. Pharm.*, 20, 2677 (1971).
CA 85, 94115 (1976).
CA 81, 120190f (1974).
CA 74, 112752f (1971).
Elford et al., *Can. Res.*, 39, 844 (1979).
van't Riet et al., *J. Med. Chem.*, 22, 589 (1979).
Elford et al., *AACR Abstracts* 601, Mar. 1979.
Elford *AACR Abstracts* 707, Mar. 1977.
Elford et al., *AACR Abstracts* 750, Mar. 1978.
van't Riet et al., *J. Pharm. Sci.*, 69, 856 (1980).
Elford et al., *Advances in Enzyme Regulation*, 19, 151 (1981).
Child et al., *Can. J. Res.*, 17, 1455 (1971).

*Primary Examiner*—Paul J. Killos
*Attorney, Agent, or Firm*—James L. Rowe; Arthur R. Whale

[57] ABSTRACT

Di, tri and tetrahydroxybenzohydroxamic acids, amides and the corresponding di, tri and tetrahydroxy substituted phenylalkanohydroxamic acids, amides and phenyl esters, ribonucleotide reductase inhibitors.

5 Claims, No Drawings

HYDROXYBENZOHYDROXAMIC ACIDS, BENZAMIDES AND ESTERS AND RELATED COMPOUNDS AS RIBONUCLEOTIDE REDUCTASE INHIBITORS

CROSS-REFERENCE

This application is a continuation-in-part of our copending application Ser. No. 247,171 filed Mar. 24, 1981, U.S. Pat. No. 4,394,389 which was a continuation-in-part of our then copending application Ser. No. 16472 filed Mar. 1, 1979, now U.S. Pat. No. 4,263,322 issued Apr. 21, 1981.

BACKGROUND OF THE INVENTION

There has been considerable interest in the synthesis and testing of hydroxy-substituted benzohydroxamic acids, particularly as antimicrobial or antitumor agents. The leading research group in this area had been headed by Glen R. Gale. In 1966, Gale presented a paper in *Proc. Soc. Exptl. Biol. Med.*, 122, 1236 (1966) on the selective inhibition of DNA synthesis by salicylhydroxamic acid. He reported that cells which had been preincubated with salicylhydroxamic acid for up to two hours showed only a slight depression of RNA and protein synthesis. Gale and Hynes reported in *J. Med. Chem.*, 11, 191 (1968) on a similar activity of other arylhydroxamic acids including 3-hydroxy, 4-hydroxy, 2,6-dihydroxy, 2,3-dihydroxy, 3,5-diamino, 4-amino and 3-aminobenzohydroxamic acids. The compounds were tested for their ability to inhibit DNA synthesis in Ehrlich ascites tumor cells in vitro. The authors confirmed the selective inhibition of DNA synthesis by salicylhydroxamic acid. Benzohydroxamic acid was found to inhibit RNA synthesis but the corresponding benzamide was found to be totally inactive. 3,5-Diaminobenzohydroxamic acid and 4-aminobenzohydroxamic acid were said to display relative selectivity against DNA synthesis, but only after exposure of the cells to the agent for 1–2 hours. 2,3-Dihydroxybenzohydroxamic acid was said to show a marked selectivity against DNA synthesis with a greater inhibition than that produced by salicylhydroxamic acid. 3-Aminobenzohydroxamic acid was reported as completely inhibiting DNA synthesis but accompanied by 50 percent depression of RNA and protein synthesis.

The authors concluded as follows: "[t]he most active and selective compounds were, thus, those with hydroxyl substituents in the 2 and 2,3-positions on the aryl ring, while addition of the same group to the 4-position yielded a virtually inactive compound. Relatively selective but less active compounds were those with amino groups in the 4 and 3,5-positions."

Howle and Gale publishing in *Proc. Soc. Exptl. Biol. Med.*, 131, 697 (1969) [same as *Chemical Abstracts* 71, 57006b (1969)] describe the effects of certain hydroxamic acids on bacterial and plant L-glutamate 1-carboxylase. A few amino and hydroxy-substituted benzoylhydroxamic acids were studied. Among the new compounds reported was 2,3,4-trihydroxybenzoylhydroxamic acid.

Gale, Hynes and Smith publishing in *J. Med. Chem.*, 13, 571 (1970) described the synthesis of additional arylhydroxamic acids which inhibited the synthesis of DNA in Ehrlich ascites tumor cells. The authors commented on work performed by the National Cancer Institute, N. Greenberg—Cancer Chemotherapy National Service Center, stating that 4-hydroxybenzoylhydroxamic acid possessed significant antitumor activity in vivo against L1210 leukemia. The sole new compound prepared disclosed was 2,5-dihydroxybenzoylhydroxamic acid. The most active compound reported was 3,5-diisopropylsalicylhydroxamic acid, with another interesting structure being 4-nitrobenzoylhydroxamic acid. The 2,5-dihydroxybenzoylhydroxamic acid derivative was apparently of little interest. The authors concluded that a majority of their derivatives which were active in vitro were substituted in the 4-position in relation to the hydroxamic acid group.

The most recent paper of interest by Gale and coworkers appeared in *Biochemical Pharmacology*, 20, 2677 (1971) [same as *Chemical Abstracts*, 76 21107z (1972)]. This paper reported the results of testing 20 arylhydroxamic acids as potential antimitogenic agents. Among the compounds tested were the following benzoylhydroxamic acid derivatives: 3-hydroxy, 4-hydroxy, 4-amino, 2,3-dihydroxy, 2,4-dihydroxy, 2,5-dihydroxy, 2,6-dihydroxy, 3,5-diamino. The most active compounds tested were 4-hydroxybenzoylhydroxamic acid and the corresponding 2,3-dihydroxy compound. 4-Aminobenzoylhydroxamic acid was found to be inactive as was the 2-hydroxy-4-aminobenzoyl compound. All compounds were compared with hydroxyurea, which compound acts on susceptible cells by inhibiting DNA synthesis through suppression of the activity of ribonucleoside diphosphate reductase. Although Gale and coworkers never tested the effect of their compounds on ribonucleotide reductase, it was the conclusion of the authors that 2,3-dihydroxybenzoylhydroxamic acid probably acted by a different mechanism. The authors also concluded that there was fundamental difference in action between the 4-hydroxy and the 2,3-dihydroxy benzohydroxamic acids.

Other investigators have also been interested in the properties of hydroxy-substituted benzoic acids and benzamides. Kreuchunas, U.S. Pat. No. 2,849,480, discloses a number of derivatives of 2,3,6-trihydroxybenzoic acid such as the amide, the N-methylamide, the N,N-dimethylamide, etc. Utility of the compounds is said to be in the treatment of rheumatic fever. *Chemical Abstracts*, 81, 120190f (1974) discloses the stabilization of aromatic amines with esters or amides of gallic acid (3,4,5-trihydroxybenzoic acid). The primary amide and the N-methylamide are specifically disclosed. *Chemical Abstracts*, 85, 94115w (1978) discloses a group of 2,6-dihydroxybenzamides useful as intermediates in the preparation of the corresponding alkylcarbamoyloxy derivatives. *Chemical Abstracts*, 74, 112752f (1971) is another disclosure of 3,5-dihydroxybenzohydroxamic acid. The compound was condensed with meta-dihydroxybenzene and formaldehyde to provide a resin. Applicants' publications relating to the activity of di- and trihydroxybenzohydroxamic acids, amides and esters as ribonucleotide reductase inhibitors with antineoplastic activity include papers appearing in *Cancer Research*, 39, 844 (1979), *J. Med. Chem*, 22, 589 (1979), *Proc. Am. Assoc. Cancer Research* 18, 177 (1977), 19, 63 (1978), 20, 149 (1979), *Virginia Journal of Science*, 29, 81 (1978), and *J. Pharm. Sci.*, 69, 856 (1980).

3,4-Dihydroxybenzohydroxamic acid and 3,4,5-trihydroxybenzohydroxamic acid are not known nor are the corresponding phenylacetohydroxamic acids. Phenolic esters of certain hydroxybenzoic acids are also novel.

This invention provides a method of inhibiting the enzyme, ribonucleotide reductase, which comprises administering to a mammal carrying a tumor having a relatively high ribonucleotide reductase level an amount of a compound according to formula I below effective to inhibit ribonucleotide reductase

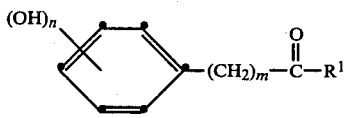

wherein $R^1$ is $NH_2$, NHOH, $NH(C_1-C_3)$alkyl, aryl-NH, $N[(C_1-C_3)alkyl]_2$ or O-phenyl; m is 0, 1, 2 or 3; and n is 2, 3 or 4, except that when m is 0, n is 2 or 3 and $R^1$ is NHOH, no OH can be ortho to the carboxyl.

Illustrative compounds useful in our novel method include the following benzohydroxamic acids, benzamides or phenyl hydroxybenzoates, compounds according to I wherein m is 0;
3,4-dihydroxybenzamide;
2,3-dihydroxybenzamide;
2,3,4-trihydroxybenzamide;
3,4,5-trihydroxybenzamide (galloamide);
2,4,5-trihydroxybenzamide;
2,3,6-trihydroxybenzamide;
phenyl 2,3-dihydroxybenzoate;
phenyl 3,4-dihydroxybenzoate;
phenyl 2,3,6-trihydroxybenzoate;
N-n-propyl 2,4,6-trihydroxybenzamide;
phenyl 3,4,5-trihydroxybenzoate (phenyl gallate);
phenyl 2,4,6-trihydroxybenzoate;
N-ethyl 3,4,5-trihydroxybenzamide.
2,3,4-trihydroxybenzohydroxamic acid;
3,4-dihydroxybenzohydroxamic acid;
3,4,5-trihydroxybenzohydroxamic acid;
3,5-dihydroxybenzohydroxamic acid;
phenyl 2,3,4-trihydroxybenzoate;
N-methyl 2,3,4-trihyroxybenzamide;
N-ethyl 3,4,5-trihydroxybenzamide;
N-n-propyl 3,4,5-trihydroxybenzamide;
N-phenyl 3,4-dihydroxybenzamide,
2,3,4,5-tetrahydroxybenzohydroxamic acid,
2,3,4,6-tetrahydroxybenzohydroxamic acid,
2,3,4,5-tetrahydroxybenzamide,
phenyl 2,3,4,5-tetrahydroxybenzoate, and the like.

Benzohydroxamic acids, benzamides and phenyl hydroxybenzoates of phenylalkanoates (I wherein m is 1, 2 or 3) are illustrated by the following compounds:
3,4-dihydroxyphenylacetamide,
β-(3,4-dihydroxyphenyl)propionamide,
β-(3,4-dihydroxyphenyl)butyramide,
β-(3,4-dihydroxyphenyl)butyrohydroxamic acid,
γ-(3,4-dihydroxyphenyl)butyrohydroxamic acid,
2,4,5-trihydroxyphenylacetohydroxamic acid,
phenyl 2,3,5-trihydroxyphenylacetate,
phenyl β-(2,3,6-trihydroxyphenyl)propionate,
phenyl γ-(2,3-dihydroxyphenyl)butyrate,
β-(3,4-dihydroxyphenyl)propionohydroxamic acid,
γ-(3,4-dihydroxyphenyl)butyramide,
2,3-dihydroxyphenylacetohydroxamic acid,
3,4,5-trihydroxyphenylacetamide,
3,4,5-trihydroxyphenylacetohydroxamic acid,
N-methyl β-(2,3,4-trihydroxyphenyl)propionamide,
N-ethyl γ-(2,3,5-trihydroxyphenyl)butyramide,
phenyl β-(3,4,5-trihydroxyphenyl)butyrate,
β-(2,3,6-trihydroxyphenyl)butyrohydroxamic,
3,4-dihydroxyphenylacetohydroxamic acid,
β-(2,4-dihydroxyphenyl)propionamide,
3,5-dihydroxyphenylacetamide,
2,3,4,5-tetrahydroxyphenylacetamide,
2,3,4,6-tetrahydroxyphenylpropionohydroxamic acid,
phenyl 2,3,4,5-tetrahydroxyphenylacetate, and the like.

In the above formula, when $R^1$ is $(C_1-C_3)$ alkyl NH or $[(C_1-C_3)alkyl]_2N$, methylamino, ethylamino, dimethylamino, n-propylamino, isopropylamino, diethylamino and the like are contemplated. The term "aryl" in "aryl-NH" includes any aromatic radical such as phenyl, thienyl, pyrimidinyl and the like as well as an aryl radical substituted with one or more standard substituting groups such as halo (Cl, Br, I, F) lower alkyl (methyl, ethyl, propyl), lower alkoxy (methoxy, ethoxy), nitro, cyano etc.

A particularly useful, and therefore preferred, method of inhibiting ribonuclease reductase employs compounds of the following structure II

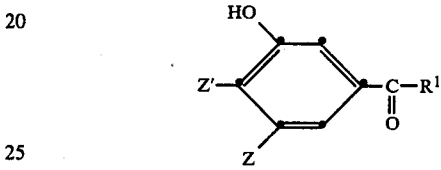

wherein Z and Z' are H or OH, at least one being OH and $R^1$ is NHOH or phenyl. Among compounds having the above structure, we specially prefer to use those compounds wherein $R^1$ is NHOH; i.e., the benzohydroxamic acids. We also prefer to use compounds in which two hydroxyls in the phenyl ring are vicinal; i.e., compounds containing a 3,4-dihydroxyphenyl or a 3,4,5-trihydroxyphenyl group.

This invention also provides certain novel compounds; specifically, it provides compounds according to the above formula in which $R^1$ is NHOH, compounds according to I in which $R^1$ is O-phenyl and compounds in which m is 1, 2 or 3. In addition, in a preferred aspect of this invention, there are provided compounds in which n is 2 or 3, two of the hydroxyl groups are at the 3 to 4 carbons of the benzene ring and m is 0. A particularly preferred group included those compounds having the above structural features in which $R^1$ is NHOH and m is 0, particularly 3,4-dihydroxybenzohydroxamic acid and 3,4,5-trihydroxybenzohydroxamic acid.

The novel compounds of this invention according to formula I above in which R is NHOH and m is 0 are prepared by reacting the corresponding ester with hydroxylamine in the presence of sodium hydroxide and sodium sulfite. The following examples illustrate the preparation of hydroxamic acids.

EXAMPLE 1

Preparation of Hydroxybenzohydroxamic acids

One-half mol of sodium hydroxide as a 25% aqueous solution was added slowly to a mixture of 0.1 mol of hydroxylamine sulfate $[(NH_2OH)_2 \cdot H_2SO_4]$ and 100 g. of ice. Next 2 g. of sodium sulfite and 0.1 mol of a particular methyl (hydroxyl substituted) benzoate were added. The reaction was stirred at room temperature in a covered flask until the ester dissolved. It was then allowed to remain overnight at 45° C. (or for two days at ambient temperature). The reaction mixture was acidified with 25% aqueous sulfuric acid with external cooling to pH=6.0. Frequently, part of the hydroxamic acid prepared in the above procedure precipitated at this point. However, in all instances, the aqueous solvent was evaporated under reduced pressure and the residue extracted with hot methanol and filtered. Evaporation of the methanol from the filtrate left the hydroxamic acid as a residue. This residue was combined with the initial precipitate, a solution of the combined hydroxamic acids decolorized with charcoal and the hydroxamic acid recrystallized from hot water.

The following table gives the physical constants of several hydroxybenzohydroxamic acids prepared by the above procedure.

TABLE 1

| Name of Compound | M.P. °C. |
|---|---|
| 2,3-dihydroxybenzohydroxamic acid[a] | 218 dec |
| 2,4-dihydroxybenzohydroxamic acid[a] | 178 dec |
| 2,5-dihydroxybenzohydroxamic acid[a] | 216 dec |
| 2,6-dihydroxybenzohydroxamic acid[a] | 215 dec |
| 3,4-dihydroxybenzohydroxamic acid[c] | 174 dec |
| 3,5-dihydroxybenzohydroxamic acid[a] | 230 dec |
| 2,3,4-trihydroxybenzohydroxamic acid[b] | 201 dec |
| 3,4,5-trihydroxybenzohydroxamic acid[a] | 230 dec |

[a] recrystallized from $H_2O$
[b] recrystallized from $H_2O$—MeOH
[c] recrystallized from ethanol-ethyl acetate
dec = with decomposition The phenyl esters ($R^1$=O-phenyl) coming within the scope of formula I are prepared from the corresponding acid and phenylchloride in the presence of an alkali metal hydroxide. Standard esterification procedures (phenol plus acid) can also be used provided a large excess of phenol is employed. The preparation of these phenyl esters is illustrated by the following example:

EXAMPLE 2

A reaction mixture was prepared containing 15 g. of anhydrous gallic acid, 8 g. of phenol, 4 ml. of phosphorous oxychloride and 200 ml. of anhydrous ether in a round-bottom flask. The mixture was heated to refluxing temperature for about 18 hours. The ether solvent was removed by evaporation. Water was added to the resulting residue and the pH of the aqueous layer adjusted to about 5 by the addition of dilute aqueous sodium hydroxide. Phenyl gallate, being insoluble at pH=5, separated and was extracted with ether. The ether extracts were separated and dried and the ether removed therefrom by evaporation. Recrystallization of the residue yielded phenyl gallate melting at about 190°–191° C.

Analysis Calculated: C, 63.41; H, 4.09; Found: C, 62.69; H, 4.14.

Compounds according to I above in which m is 1, 2 or 3 are prepared in similar fashion; i.e., the amides and hydroxamic acid derivatives are prepared from the esters. These esters are in turn either available commercially or are available synthetically as in the case of the phenyl esters by following known procedures. The preparation of one such compound is illustrated below.

EXAMPLE 3

3,4-dihydroxyphenylacetic acid was converted to the corresponding methyl ether by heating in methanolic sulfuric acid (2%) solution. Crude ester obtained from 10 g. of acid was added to a mixture of 6 g. of hydroxylamine sulfate, 2 g. of sodium sulfite and 16 g. of 50% (w/w) aqueous sodium hydroxide. After standing for 18 hours at room temperature, the mixture was neutralized (pH=6.0) with dilute (10%) sulfuric acid. Volatile constituents were removed in vacuo. The resulting residue was extracted with hot ethanol. The ethanol was evaporated and the residue, containing 3,4-dihydroxyphenylacetohydroxamic acid formed in the above reaction, was recrystallized from hot isopropanol to yield crystals melting at 140°–5° C.

Preparation of starting materials

The di and trihydroxybenzoic acid esters employed as starting materials in most of the above syntheses were themselves prepared from the corresponding di or trihydroxybenzoic acid according to the following procedure: one-tenth mol of the di or trihydroxybenzoic acid was refluxed for about 24 hours with 100 ml. of methanol containing 2% (v/v) concentrated sulfuric acid. At this time, the excess methanol was removed by evaporation under reduced pressure and the residual esters suspended in water. The esters were isolated therefrom by published procedures. The following di or trihydroxybenzoic acid methylesters are known: 2,3-dihydroxy, 2,5-dihydroxy, 3,4-dihydroxy, 3,4,5-dihydroxy, as is methyl 3,4-dihydroxyphenylacetate.

2,3,4-Trihydroxybenzoic acid was not commercially available, but was readily prepared by heating pyrogallol with sodium bicarbonate (20 g. to 30 g.) in a mixture of 30 ml. of water and 20 ml. of mesitylene. Acidification of the resulting suspension with concentrated aqueous hydrochloric acid yielded 2,3,4-trihydroxybenzoic acid melting at about 220° C. with decomposition, (literature melting point=221° C.) Methyl 2,3,4-trihydroxybenzoate was prepared by heating the acid with a methanol-sulfuric acid mixture. The compound thus prepared melted at 151° C. (compared to a literature melting point of 153° C.). The methyl ester of 2,6-dihydroxybenzoic acid was synthesized by preparing the silver salt of the acid and treating it with methyl iodide. Methyl 2,6-dihydroxybenzoic melted at 67° C., (published melting point=67°–68° C.).

As stated above, the compounds represented by formula I above have the ability to inhibit ribonucleotide reductase, an enzyme involved in the reductive conversion of ribonucleotides to deoxyribonucleotides. This enzymatic reaction is a rate controlling step in the biosynthetic pathway leading to DNA and cell replication. In general, the ribonucleotide reductase level is closely correlated with cellular replication. Thus, it is not surprising that the compounds of this invention, which are potent ribonucleotide reductase inhibitors, are also capable of prolonging the life of mice carrying transplanted tumors since replication of tumor cells is equally inhibited. In particular, we have found that administration of a compound of this invention represented by formula I above prolongs the life of mice inoculated with L1210 leukemia, a tumor not ordinarily susceptible to chemotherapy. In addition, the compounds have demonstrated activity against other transplanted tumors; i.e., Lewis Lung, X-5563 lymphoma and 755 adenocarcinoma, $B_{16}$ melanoma, C-8 colon, breast and human xenographs.

The results of several biological tests of compound according to formula I are incorporated in the following tables.

Table 2 gives ribonucleotide reductase data for certain compounds of formula I. In the table, column 1 gives the substitution pattern in the benzene ring, column 2, the $R^1$ group, column 3, the $ID_{50}$ (inhibitory dose in micromolar concentration which inhibits ribonucleotide reductase by 50%), column 4, the average percent (± standard error) increase in the life span (ILS) of 8 treated mice inoculated with L1210 leukemia compared with 8 control mice also inoculated with L1210. The daily dose level of the drug which was administered for 8 days is indicated in column 5. Table 3 gives the relative potency of the compounds represented by formula I above as inhibitors of ribonucleotide reductase compared to hydroxyurea whose potency was given an arbitrary value of 1.0. In table 3, column 1 gives the name of the compound and column 2 the relative inhibitory potency of each of the compounds of column 1.

TABLE 2

(OH) — [benzene ring] — C(=O)—R$^1$

| (OH) | R$^1$ | ID$_{50}$ (μM) | ILS. | Dose mg/kg |
|---|---|---|---|---|
| 2,3 | NHOH | 8 | 36 ± 11 | 200 |
| 2,4 | NHOH | 250 | 42 ± 7 | 500 |
| 2,5 | NHOH | 200 | 30 ± 14 | 300 |
| 2,6 | NHOH | 100 | 23 ± 11 | 88 |
| 3,4 | NHOH | 30 | 103 ± 15 | 600 |
| 3,5 | NHOH | 400 | 52 ± 22 | 1000 |
| 2,3,4 | NHOH | 3.5 | 30 ± 7 | 125 |
| 3,4,5 | NHOH | 10 | 53 ± 19 | 400 |
| 3,4 | NH$_2$ | 50 | 35 ± 11 | 1200 |
| 2,3,4 | NH$_2$ | 5 | 48 ± 7 | 200 |
| 3,4,5 | NH$_2$ | 10 | 42 ± 5 | 250 |
| 3,4,5 | NHCH$_3$ | 25 | 60 ± 29 | 500 |

TABLE 3

| Name of compound | Inhibitory Potency for ribonucleotide reductase |
|---|---|
| Hydroxyurea (control compound) | 1.0 |
| 3,5-dihydrobenzohydroxamic acid | 1.2 |
| 2,4-dihydroxybenzohydroxamic acid | 2.0 |
| 2,5-dihydroxybenzohydroxamic acid | 2.5 |
| 2,6-dihydroxybenzohydroxamic acid | 5.0 |
| Vicinal hydroxyls | |
| 2,3-dihydroxybenzohydroxamic acid | 63 |
| 3,4-dihydroxybenzohydroxamic acid | 17 |
| 3,4-dihydroxybenzamide | 10 |
| 3,4,5-trihydroxybenzohydroxamic acid | 50 |
| 2,3,4-trihydroxybenzohydroxamic acid | 140 |
| 3,4,5-trihydroxybenzamide | 50 |
| 2,3,4-trihydroxybenzamide | 100 |
| phenyl 3,4,5-trihydroxybenzoate | 33 |

In the above determination of ID$_{50}$'s in Table 3, ribonucleotide reductase is partially purified from Novikoff hepatoma by a procedure similar to that set forth by Elford et al. J. Biol. Chem. 245, 5228 (1970). The activity of the enzyme was measured by a slightly modified assay procedure originally developed by Reichard et al. id, 236, 1150 (1969). This procedure measures the conversion of CDP to dCDP. The assay mixture (0.34 ml.) contains 3 μCi of [$^3$H] CDP (specific activity 14–19 Ci/μmol), 3.3 μmole ATP, 5.9 μmoles magnesium chloride, 8.8 μmoles Hepes buffer at pH=7.5, 15 μmoles dithiothreitol and enzyme protein between 0.4 and 1.3 mg. Incubation was provided for forty minutes at 30° C. Ion exchange chromatography employing Dowex 50 (H$^+$) resin is used to separate the product from the substrate. The inhibitors were dissolved in water and a mixture of water and up to 1% ethanol or 2% dimethylsulfoxide, neither one of which inhibited the enzyme at these concentrations. Each inhibitor was tested at a minimum of three concentrations and the active compounds reassayed at least one additional time. ID$_{50}$'s in μmoles were estimated from graphs summarizing results for each compound.

In addition, positive experimental results obtained by testing compounds represented by formula I against five transplanted tumors in mice are set forth in Tables 4–8. The L1210 data (Table 4) are in addition to the data in Table 2. All compounds were administered once or twice daily for 9–10 days starting 24 hours after inoculation with the tumor. In tables 4–8, column 1 gives the name of the compound, column 2, the dose level, and column 3 percent increase in survival time or prolongation of life.

TABLE 4

Activity vs. L-1210 Leukemia

| name of compound | dose in mg/kg | % increase in survival time |
|---|---|---|
| galloamide | 250 | toxic |
|  | 225 | 10 |
|  | 200 | 46, 108 |
|  | 175 | 55 |
|  | 150 | 50 |
| gallohydroxamic acid | 120 | 54 |
|  | 100 | 58, 55 |
|  | 75 | 60 |
| 3,4-dihydroxybenzohydroxamic acid | 225 | 65 |
|  | 200 | 54, 141 |
|  |  | (4 survivors) |
|  | 175 | toxic |
| 2,3,4-trihydroxybenzohydroxamic acid | 25–50 | 17–21 |
| phenyl gallate | 200 | 56 |
| hydroxyurea (positive control) | 71 | 58 |
|  | 60 | 92 |
|  | 40 | 27 |
|  | 30 | 27 |
| 3,4-dihydroxyphenylacetohydroxamic acid | 606 | 57 |

TABLE 5

Activity vs. Lewis Lung

| name of compound | dose in mg/kg | % tumor inhibition |
|---|---|---|
| gallohydroxamic acid | 100 | 40 |
| galloamide | 200 | 21 |
| 3,4-dihydroxybenzohydroxamic acid | 200 | 14 |
|  | 400 | 31–58 |
| 2,3,4-trihydroxybenzohydroxamic acid | 25–50 | 13–14 |
| phenyl gallate | 50 | 2 |
|  | 200 | 14 |
| hydroxyurea (positive control) | 71 | 27 |
|  | 400 | 44 |

TABLE 6

Activity vs. L-5563 lymphoma

| Name of compound | dose in mg/kg | % inhibition |
|---|---|---|
| gallohydroxamic acid | 100 | 41 |
| galloamide | 200 | toxic |
| 3,4-dihydroxybenzohydroxamic acid | 200 | 24 |
| 2,3,4-trihydroxybenzohydroxamic acid | 25–50 | toxic |
| phenylgallate | 200 | 19 |
| hydroxyurea (positive control) | 71 | toxic |

TABLE 7

Activity vs. CA-755 adenocarcinoma

| Name of compound | Dose mg/kg | % inhibition |
|---|---|---|
| gallohydroxamic acid | 100 | 28 |
|  | 150 | 11 |
|  | 175 | 29 |
| galloamide | 200 | 38 |
| 3,4-dihydroxybenzohydroxamic acid | 100 | 16 |
|  | 200 | 25, 36 |

TABLE 7-continued

| Activity vs. CA-755 adenocarcinoma | | |
|---|---|---|
| Name of compound | Dose mg/kg | % inhibition |
| 2,3,4-trihydroxybenzohydroxamic acid | 300 | 52, toxic |
| | 25–50 | 12–18 |
| phenyl gallate | 100 | 27 |
| | 200 | 11 |
| hydroxyurea (positive control) | 71 | 27 |
| | 200 | 26 |

TABLE 8

| Activity vs. P388 Leukemia | | |
|---|---|---|
| Name of Compound | Dose in mg/kg | % Prolongation |
| 3,4,5-Trihydroxybenzo-hydroxamic acid | 225 | 79% |
| | 200 | 62% |
| 3,4-dihydroxybenzo-hydroxamic acid | 225 | 89% |
| | 200 | 51% |
| galloamide | 225 | 55% |
| | 200 | 40% |
| | 175 | 43% |

In addition, the compound 3,4-dihydroxybenzenehydroxamic acid was active against CX-1 colon xenograft using the following protocol:
0% tumor inhibition at 800 mg/kg dose level every fourth day,
14% at 400 mg/kg level and
48% at 200 mg/kg level.

3,4,5-trihydroxybenzohydroxamic acid gave the following results against the same tumor using the same protocol.
44% inhibition at 800 mg/kg
40% inhibition at 400 mg/kg
17% inhibition at 200 mg/kg The same drug showed excellent prolongation of life for mice inoculated with P-388 leukemia: 23–53% at doses ranging from 50–400 mg/kg every fifth day. The same two compounds were effective in inhibiting the growth of the following transplanted tumors—B$_{16}$ melanoma, M-1 human breast xenograft, LX-1 human lung xenograft, CD8F mammary tumor and colon 38 tumor—as follows:

3,4-dihydroxybenzohydroxamic acid

| CD8F, | 300 mg/kg | 52% | inhibition |
| | 600 mg/kg | 11% | " |
| C8 | 400 mg/kg | 52% | " |
| | 200 mg/kg | 15% | " |
| | 100 mg/kg | 8% | " |
| | 50 mg/kg | 12% | " |
| B16 | 400 mg/kg | 41% | increase in survival |
| | 200 mg/kg | 24–25% | " |
| LX-1 | 800 mg/kg | 27% | inhibition |
| | 400 mg/kg | 26% | " |
| | 200 mg/kg | 0% | " |

3,4,5-trihydroxybenzohydroxamic acid

| CD8F | 600 mg/kg | 22% | inhibition |
| | 300 mg/kg | 0% | " |
| C8 | 800 mg/kg | 60% | " |
| | 400 mg/kg | 17% | " |
| | 200 mg/kg | 32% | " |
| | 100 mg/kg | 30% | " |
| | 50 mg/kg | 20% | " |
| B16 | 200 mg/kg | 18% | increase in survival |
| | 100 mg/kg | 14% | " |
| M-1 | 1600 mg/kg | 41% | inhibition |
| | 800 mg/kg | 56% | " |
| | 400 mg/kg | 21% | " |
| | 200 mg/kg | 69% | " |

In a series of studies against L-1210 leukemia, in addition to those studies set forth in Table 2 and 4, 3,4-dihydroxybenzohydroxamic acid gave the following increases in survival times at the dose levels specified. Drug was administered daily for nine days.

| Dose mg/kg | % increase in survival |
|---|---|
| 600 | 54, 64 |
| 480 | 106, 87, 67 |
| 400 | 67 |
| 384 | 62, 85 |
| 336 | 55 |
| 307 | 67, 76 |
| 200 | 67 |
| 245 | 45, 68 |
| 235 | 39 |
| 196 | 52 |
| 164 | 21 |
| 100 | 37 |
| 50 | 25 |
| 25 | 15 |

Similar data for 3,4,5-trihydroxybenzohydroxamic acid are as follows:

| Dose | % increase in survival time |
|---|---|
| 800 | 16 |
| 400 | 0, 4 |
| 200 | 54, 56 |
| 100 | 17, 39 |
| 50 | 27, 29 |

2,3,4-trihydroxybenzohydroxamic acid

| Dose mg/kg | % increase in survival time |
|---|---|
| 200 | Toxic |
| 100 | 16 |
| 50 | 8 |
| 25 | 10 |

The above data clearly show the enhanced antitumor activity of trihydroxybenzohydroxamic acid where the hydroxy groups are vicinal but no hydroxyl is ortho. Similar data are available for the vicinal dihydroxybenzohydroxamic acids with and without an ortho-hydroxy substituent in an L-1210 leukemic test in mice as follows:

3,4-dihydroxybenzohydroxamic acid

| Dose mg/kg | % increase in survival time |
|---|---|
| 800 | Toxic |
| 643 | 65 |
| 600 | 94, 103 |
| 543 | 77 |
| 500 | 84 |
| 453 | 125 |
| 300 | 56 |
| 100 | 25 |

2,3-dihydroxybenzohydroxamic acid

| Dose mg/kg | % increase in survival time |
| --- | --- |
| 500 | Toxic |
| 450 | about 0 |
| 300 | about 0, toxic |
| 200 | 6, 36 |

In a direct side-by-side comparison with L-1210 leukemia, the following results were obtained.

3,4-dihydroxybenzohydroxamic acid

| Dose mg/kg | % increase in survival time |
| --- | --- |
| 500 | 70 |
| 250 | 32 |

2,3-dihydroxybenzohydroxamic acid

| Dose mg/kg | % increase in survival time |
| --- | --- |
| 250 | 16 |
| 125 | 0 |

The superiority as anti-leukemic drugs of the 3,4 and 3,4,5 hydroxysubstitution patterns in the novel benzhydroxamic derivatives of this invention compared with the 2,3 and 2,3,4 hydroxy substitution patterns of the prior art compounds is clearly established by the above data.

We claim:

1. A method of inhibiting ribonucleotide reductase which comprises administering to a mammal carrying a tumor having a relatively high ribonucleotide reductase level, an amount of a compound according to the following formula effective to inhibit ribonucleotide reductase

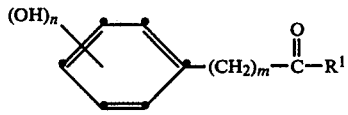

wherein n is 2, 3 or 4, m is 1, 2 or 3 and $R^1$ is $NH_2$, NHOH, $NH(C_1-C_3)alkyl$, $N[(C_1-C_3)alkyl]_2$, $aryl-NH_2$ or O-phenyl except that when n is 2 or 3, m is 0 and $R^1$ is NHOH, no OH can be ortho to the carboxyl.

2. A method according to claim 1 in which two of the OH groups in the phenyl ring are vicinal.

3. A method according to claim 1 in which $R^1$ is NHOH.

4. A compound of the formula

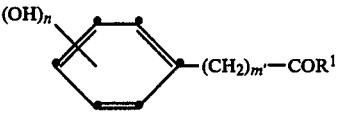

in which n is 2 or 3, m' is 1, 2 or 3 and $R^1$ is NHOH, or o-phenyl.

5. A compound according to claim 4, said compound being 3,4-dihydroxyphenylacetohydroxamic acid.

* * * * *